(12) United States Patent
Lee et al.

(10) Patent No.: US 7,550,570 B2
(45) Date of Patent: *Jun. 23, 2009

(54) 4,7-DICHLORORHODAMINE DYES LABELED POLYNUCLEOTIDES

(75) Inventors: Linda G. Lee, Palo Alto, CA (US); Scott C. Benson, Oakland, CA (US); Barnett B. Rosenblum, San Jose, CA (US); Sandra L. Spurgeon, San Mateo, CA (US); Ronald J. Graham, Pleasanton, CA (US)

(73) Assignee: Applied Biosystems, LLC., Foster City, CA (US)

( * ) Notice: Subject to any disclaimer, the term of this patent is extended or adjusted under 35 U.S.C. 154(b) by 338 days.

This patent is subject to a terminal disclaimer.

(21) Appl. No.: 10/788,660

(22) Filed: Feb. 26, 2004

(65) Prior Publication Data

US 2005/0112781 A1     May 26, 2005

(51) Int. Cl.
C07G 3/00 (2006.01)
C07H 19/04 (2006.01)
C12Q 1/68 (2006.01)

(52) U.S. Cl. .................. 536/4.1; 536/26.6; 435/6
(58) Field of Classification Search ............. 536/4.1, 536/26.6; 435/6
See application file for complete search history.

(56) References Cited

U.S. PATENT DOCUMENTS

| | | | |
|---|---|---|---|
| 4,318,846 | A | 3/1982 | Khanna et al. |
| 4,622,400 | A | 11/1986 | Hammond |
| 4,855,225 | A | 8/1989 | Fung et al. |
| 4,965,349 | A | 10/1990 | Woo et al. |
| 5,188,934 | A | 2/1993 | Menchen et al. |

(Continued)

FOREIGN PATENT DOCUMENTS

| | | |
|---|---|---|
| CH | 12433/70 | 2/1973 |
| DE | 45263 | 11/1887 |
| DE | 47451 | 11/1887 |
| DE | 108347 | 11/1898 |
| DE | 2049503 | 4/1971 |

(Continued)

OTHER PUBLICATIONS

Beilstein, "Handbuch der Organischen Chemie", Dec. 18, 1997, col. XIX, pp. 348-349.
Arden et al., "Fluorescence and lasing properties of rhodamine dyes", *Journal of Luminescense*, 1991, 48 & 49:352-358.
Ioffe et al., "Studies in the Field of Rhodamine Dyes and Compounds Related to Them", *Zhurnal Organicheskol Khimii*, Feb. 1965, 1(2): 336-339.

Vogel et al., "Structural Relaxation of Rhodamine Dyes with Different N-Substitution Patterns: A Study of Fluorescence Decay Times and Quantum Yielda", *Chemical Physics Letters*, Jun. 17, 1988, 147(5): 452-460.

*Primary Examiner*—Jezia Riley
(74) *Attorney, Agent, or Firm*—Dechert LLP

(57) ABSTRACT

A set of 4,7-dichlororhodamine compounds useful as fluorescent dyes are disclosed having the structures

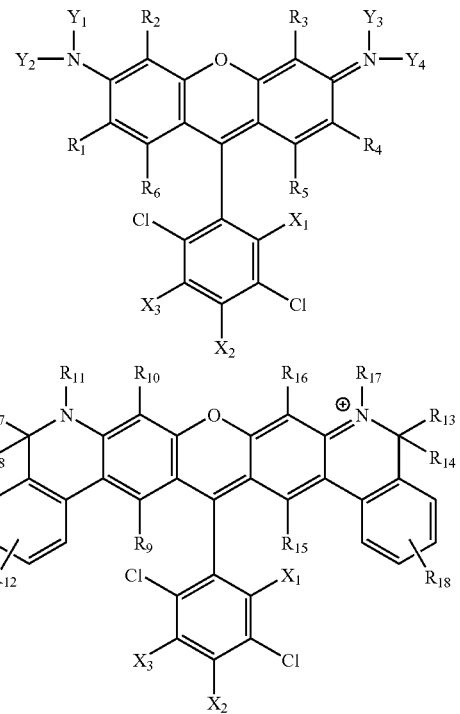

wherein $R_1$-$R_6$ are hydrogen, fluorine, chlorine, lower alkyl, lower alkene, lower alkyne, sulfonate, sulfone, amino, amido, nitrile, lower alkoxy, linking group, or, when taken together, $R_1$ and $R_6$ is benzo, or, when taken together, $R_4$ and $R_5$ is benzo; $R_7$-$R_{10}$, $R_{12}$-$R_{16}$ and $R_{18}$ may be hydrogen, fluorine, chlorine, lower alkyl, lower alkene, lower alkyne, sulfonate, sulfone, amino, amido, nitrile, lower alkoxy, linking group; $R_{11}$ and $R_{17}$ may be hydrogen, lower alkyl, lower alkene, lower alkyne, phenyl, aryl, linking group; $Y_1$-$Y_4$ are hydrogen, lower alkyl, or cycloalkyl, or, when taken together, $Y_1$ and $R_2$, $Y_2$ and $R_1$, $Y_3$ and $R_3$, and/or $Y_4$ and $R_4$ is propano, ethano, or substituted forms thereof; and $X_1$-$X_3$ taken separately are hydrogen, chlorine, fluorine, lower alkyl, carboxylate, sulfonate, hydroxymethyl, and linking group, or any combinations thereof. In another aspect, the invention includes reagents labeled with the 4,7-dichlororhodamine dye compounds, including deoxynucleotides, dideoxynucleotides, and polynucleotides. In an additional aspect, the invention includes methods utilizing such dye compounds and reagents including dideoxy polynucleotide sequencing and fragment analysis methods.

52 Claims, No Drawings

U.S. PATENT DOCUMENTS

| | | |
|---|---|---|
| 5,256,799 A | 10/1993 | Field et al. |
| 5,283,336 A | 2/1994 | Field et al. |
| 5,366,860 A | 11/1994 | Bergot et al. |
| 5,750,409 A | 5/1998 | Herrmann et al. |
| 5,770,716 A | 6/1998 | Khan et al. |
| 5,847,162 A | 12/1998 | Lee et al. |
| 6,017,712 A | 1/2000 | Lee et al. |
| 6,025,505 A | 2/2000 | Lee et al. |
| 6,080,852 A | 6/2000 | Lee et al. |

FOREIGN PATENT DOCUMENTS

| | | |
|---|---|---|
| DE | 2049527 | 4/1971 |
| DE | 3425631 A1 | 1/1986 |
| EP | 0 252 683 | 7/1987 |
| EP | 333 649 B1 | 6/1994 |
| GB | 1286885 | 8/1972 |
| JP | 2-3888 | 1/1990 |
| WO | WO 91/03476 | 3/1991 |
| WO | WO 91/05060 | 4/1991 |
| WO | WO 91/07507 | 5/1991 |
| WO | WO 94/05888 | 3/1994 |
| WO | WO 94/06812 A1 | 3/1994 |
| WO | WO 97/36960 | 10/1997 |
| WO | WO 97/49769 | 12/1997 |
| WO | WO 99/27020 | 6/1999 |

4,7-DICHLORORHODAMINE DYES LABELED POLYNUCLEOTIDES

FIELD OF THE INVENTION

This invention relates generally to fluorescent dye compounds useful as molecular probes. More specifically, this invention relates to 4,7-dichlororhodamine dyes useful as fluorescent labeling reagents.

REFERENCES

ABI PRISM™ 377 DNA Sequencer User's Manual, *Rev. A*, Chapter 2, The Perkin-Elmer Corporation, Foster City, Calif. (p/n 903433) (1995).
Bergot, J. B., etal., U.S. Pat. No. 5,366,860 (1994)
Bergstrom, etal., *JACS*, 111: 374-375 (1989)
Caskey etal., U.S. Pat. No. 5,364,759 (1994)
Connell etal., *Biotechniques*, 5:342-348 (1987)
Eckstein ed., *Oligonucleotides and Analogs*, Chapters 8 and 9, IRL Press (1991)
Eckstein, *Oligonucleotides and Analogues*, IRL Press (1991)
Fung etal., U.S. Pat. No. 4,757,141 (1988)
Fung etal., U.S. Pat. No. 4,855,225 (1989)
Gait, *Oligonucleotide Synthesis*, IRL Press (1990)
Gebeyehu etal, *Nucleic Acids Research*, 15:4513-4535 (1987)
Gibson etal., *Nucleic Acids Research*, 15:6455-6467 (1987)
Haralambidis etal, *Nucleic Acids Research*, 15:4856-4876 (1987)
Haugland, *Molecular Probes Handbook of Fluorescent Probes and Research Chemicals*, Molecular Probes, Inc. (1992)
Herrmann, R., Josel, H., Drexhage, K. Arden, J., U.S. Pat. No. 5,750,409, issued May 12, 1998.
Hermanson, *Bioconjugate Techniques*, Academic Press (1996)
Hobbs etal., *J. Org. Chem.*, 54:3420 (1989)
Hobbs etal., U.S. Pat. No. 5,151,507 (1992)
Hunkapiller, etal., U.S. Pat. No. 4,811,218 (1989)
Innis etal. eds., *PCR Protocols*, Academic Press (1990)
Ju etal., *Proc. Natl. Acad. Sci. USA* 92:4347-4351 (1995).
Kasai, etal., *Anal. Chem.*, 47:34037 (1975)
Khan, S., Menchen, S., Rosenblum, B. "Substituted propargylethoxyamido nucleosides, oligonucleotides and methods for using same", U.S. Pat. No. 5,770,716, issued Jun. 23, 1998
Khan, S., Menchen, S., Rosenblum, B; "Propargylethoxyamino nucleotides", U.S. Pat. No. 5,821,356, issued Oct. 13, 1998
Khan, S. etal, "Nucleotides including a rigid linker", Ser. No. 09,172,789, filing date Oct. 14, 1998.
Khanna, etal., U.S. Pat. No. 4,318,846 (1988)
Lee etal. *Nucleic Acids Research*, 21:3761-3766 (1993)
Lee, L., Benson, S., Rosenblum, B., Spurgeon, S., Cassel, J. and Graham, R., "4,7-Dichlororhodamine Dyes", U.S. Pat. No. 5,847,162, issued Dec. 8, 1998
Madabhushi, etal., International Patent Application No. WO US94/13852 (1994)
Maniatis, *Methods in Enzymology*, 65:299-305 (1980)
Menchen, etal., U.S. Pat. No. 5,188,934 (1993)
Mullis, U.S. Pat. No. 4,683,202 (1987)
Nelson etal., *Nucleosides and Nucleotides*, 5(3):233-241 (1986)
Nelson, et al., *Nucleic Acids Research* 20(23):6253-6259 (1992a)
Nelson, U.S. Pat. No. 5,141,813 (1992b)
Nelson, U.S. Pat. No. 5,401,837 (1995)
Orgel etal., *Nucleic Acids Research* 11(18):6513 (1983)
Osterman, *Methods of Protein and Nucleic Acid Research*, Vol. 1 Springer-Verlag (1984)
Pringle etal., *DNA Core Facilities Newsletter*, 1:15-21 (1988)
Prober etal., *Science*, 238:336-341 (1987)
Rickwood and Hames, eds., *Gel Electrophoresis of Nucleic Acids: A Practical Approach*, IRL Press (1981)
Sanger, etal., *Proc. Natl. Acad. Sci. USA* 74:5463-5467 (1977)
Scheit, *Nucleotide Analogs*, John Wiley (1980)
Smith etal., *Nucleic Acids Research*, 113:2399-2412 (1985)
Smith etal., U.S. Pat. No. 5,118,800 (1992)
Steiner ed., *Excited States of Biopolymers*, Plenum Press (1983)
Stryer, *Biochemistry*, W. H. Freeman (1981)
Vos etal., Nucleic Acids Research, 23(21):4407-4414 (1995)
Vogel, A, Rettig, W., Sens, R. Drexhage, K, Chemical Physics Letters, 147:452-60 (1988)
Ward, etal., U.S. Pat. No. 5,559,767 (1995)
Webber, U.S. Pat. No. 5,075,217 (1991)
Wheeless etal, *Flow Cytometry: Instrumentation and Data Analysis*, pgs. 21-76, Academic Press (1985)
Woo, etal., U.S. Pat. No. 5,231,191 (1993)

BACKGROUND

The non-radioactive detection of biological analytes is an important technology in modern analytical biotechnology. By eliminating the need for radioactive labels, safety is enhanced and the environmental impact of reagent disposal is greatly reduced, resulting in decreased costs for analysis. Examples of methods utilizing such non-radioactive detection methods include DNA sequencing, oligonucleotide probe methods, detection of polymerase-chain-reaction products, immunoassays, and the like.

In many applications the independent detection of multiple spatially overlapping analytes in a mixture is required, e.g., single-tube multiplex DNA probe assays, immuno assays, multicolor DNA sequencing methods, and the like. In the case of multi-loci DNA probe assays, by providing multicolor detection, the number of reaction tubes may be reduced thereby simplifying the experimental protocols and facilitating the manufacturing of application-specific kits. In the case of automated DNA sequencing, multicolor labeling allows for the analysis of all four bases in a single lane thereby increasing throughput over single-color methods and eliminating uncertainties associated with inter-lane electrophoretic mobility variations.

Multiplex detection imposes a number of severe constraints on the selection of dye labels, particularly for analyses requiring an electrophoretic separation and treatment with enzymes, e.g., DNA sequencing. First, it is difficult to find a collection of dyes whose emission spectra are spectrally resolved, since the typical emission band half-width for organic fluorescent dyes is about 40-80 nanometers (nm) and the width of the available spectrum is limited by the excitation light source. Second, even if dyes with non-overlapping emission spectra are found, the set may still not be suitable if the respective fluorescent efficiencies are too low. For example, in the case of DNA sequencing, increased sample loading cannot compensate for low fluorescence efficiencies (Pringle). Third, when several fluorescent dyes are used concurrently, simultaneous excitation becomes difficult because the absorption bands of the dyes are widely separated. Fourth, the charge, molecular size, and conformation of the dyes must not adversely affect the electrophoretic mobilities of the fragments. Finally, the fluorescent dyes must be compatible with the chemistry used to create or manipulate the fragments, e.g., DNA synthesis solvents and reagents, buffers, polymerase enzymes, ligase enzymes, and the like.

Because of these severe constraints only a few sets of fluorescent dyes have been found that can be used in multi-color applications, particularly in the area of four-color DNA sequencing (Smith 1992, 1995; Prober, Connell).

One class of fluorescent dyes particularly useful in multi-color applications are the rhodamine dyes, e.g., tetramethyl-rhodamine (TAMRA), rhodamine X (ROX), rhodamine 6G (R6G), rhodamine 110 (R110), and the like (Bergot). Rhodamine dyes are particularly attractive relative to fluorescein dyes because (1) rhodamines are typically more photostable than fluoresceins, (2) rhodamine-labeled dideoxynucleotides are better substrates for thermostable polymerase enzymes, and (3) the emission spectra of rhodamine dyes is significantly to the red (higher wavelength) of fluoresceins.

However, one important drawback of presently available rhodamine dyes in the context of multiplex detection methods is the relatively broad emission spectrum of such dyes. This broad emission spectrum results in poor spectral resolution between spectrally neighboring dyes thereby making the multicomponent analysis of such dye combinations difficult. The fluorescence emission spectra shown in FIG. 7A demonstrate this high degree of spectral overlap. A second drawback of currently available rhodamine dyes is that their absorption spectrum does not match the wavelength of currently available solid state frequency-doubled green diode lasers, e.g., neodymium solid-state YAG lasers, which have an emission line at approximately 532 mm. It is highly advantageous to use such lasers because of their compact size, long useful life, and efficient use of power.

SUMMARY

The present invention is directed towards our discovery of a class of 4,7-dichlororhodamine dyes useful as molecular probes.

It is an object of the invention to provide a class of rhodamine dyes which have emission spectra which are substantially narrower than presently available rhodamine dyes.

It is another object of the invention to provide a class of rhodamine dyes which have an absorption spectrum shifted to the red as compared to existing rhodamine dyes.

In a first aspect, the foregoing and other objects of the invention are achieved by a compound having the formula:

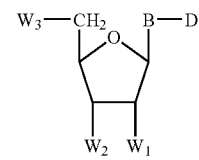

In a second aspect, the invention includes a compound having the formula:

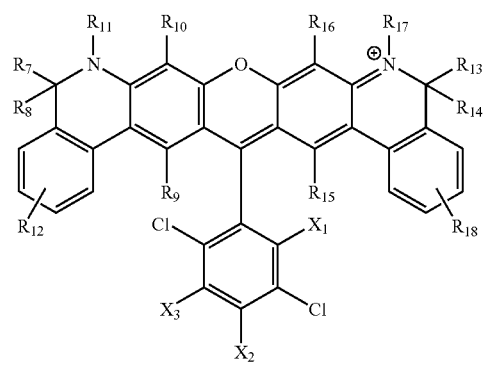

In a third aspect the invention includes a labeled nucleotide having the formula:

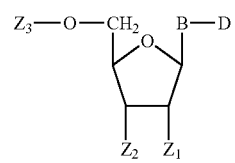

In a fourth aspect the invention includes a labeled polynucleotide containing a nucleotide having the formula:

The linkage linking B, and D is attached to D at one of positions $R_1$-$R_6$ or $X_1$-$X_3$. Preferably, the linkage linking B and D is attached to D at one of positions $X_2$ or $X_3$. In a particularly preferred embodiment, the linkage is

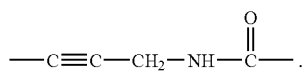

If B is a purine, the linkage is attached to the 8-position of the purine. If B is 7-deazapurine, the linkage is attached to the 7-position of the 7-deazapurine. If B is pyrimidine, the linkage is attached to the 5-position of the pyrimidine.

In a fifth aspect, the present invention includes a method of polynucleotide sequencing, such method including the following steps. Forming a mixture of a first, a second, a third, and a fourth class of polynucleotides such that each polynucleotide in the first class includes a 3'-terminal dideoxyadenosine and is labeled with a first dye, each polynucleotide in the second class includes a 3'-terminal dideoxycytidine and is labeled with a second dye, each polynucleotide in the third class includes a 3'-terminal dideoxyguanosine and is labeled with a third dye, and, each polynucleotide in the fourth class includes a 3'-terminal dideoxythymidine and is labeled with a fourth dye. The dyes are selected such that one of the first second, third, or fourth dyes is a 4,7-dichlororhodamine dye of the invention, the other of the dyes being spectrally resolvable from the 4,7-dichlororhodamine dye and from each other. Electrophoretically separating the polynucleotides thereby forming bands of similarly sized polynucleotides, illuminating the bands with an illumination beam capable of causing the dyes to fluoresce, and, identifying th classes of the polynucleotides in the bands by the fluorescence spectrum of the dyes.

These and other aspects, objects, features, and advantages of the present invention will become better understood with reference to the following description, drawings, and appended claims.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, the present invention comprises a novel class of 4,7-dichlororhodamine compounds useful as fluorescent dyes, reagents employing such dyes as molecular labels, and methods utilizing such dyes and reagents in the area of analytical biotechnology. The compounds of the present invention find particular application in the area of multicolor fluorescent DNA sequencing and fragment analysis.

The invention is based in part on the discovery that the fluorescent properties of 4,7-dichlororhodamines and related dyes are highly favorable for use as molecular probes. Their emission band widths are generally 20-30 percent narrower than analogs lacking the 4,7-dichloro derivatives, and, their emission and absorption maxima are at wavelengths generally about 10-30 nm higher than analogs lacking the 4,7-dichloro derivatives.

I. Definitions

Unless stated otherwise, the following terms and phrases as used herein are intended to have the following meanings:

"Linking group" (L) refers to a functionality capable of reacting with a "complementary functionality" attached to a reagent, such reaction forming a "linkage" connecting a dye to a reagent. The particular linking group used depends on the nature of the complementary functionality and the type of linkage desired. In some cases, the linking group must be activated prior to reaction with a complementary functionality, e.g., the activation of a carboxylate linking group with dicyclohexylcarbodiimide and N-hydroxysuccinimide to form a N-hydroxysuccinimide (NHS) ester. Preferably, whenever the complementary functionality is amine, the linking group of the invention is isothiocyanate, isocyanate, acyl azide, NHS ester, sulfonyl chloride, aldehyde or glyoxal, epoxide, carbonate, aryl halide, imidoester, carbodiimide, anhydride, 4,6-dichlorotriazinylamine, or other active carboxylate. Preferably, whenever the complementary functionality is sulfhydryl, the linking group is haloacetyl, alkyl halide, maleimide, halo acetyl, aziridine, acryloyl, arylating agent, e.g., fluorobenzene, and the like. When the complementary functionality is carboxylate, the linking group is preferably diazoalane, diazoacetyl, carbonyldiimidazole, and carbodiimide (Hermanson). In a particularly preferred embodiment, the linking group is an activated NHS ester which reacts with an amine complementary functionality, where to form the activated NHS ester, a dye of the invention including a carboxylate linking group is reacted with dicyclohexylcarbodiimide and N-hydroxysuccinimide to form the NHS ester (Khanna; Kasai). Table 1 below shows a sampling of representative linking groups along with compatible complementary functionalities and resulting linkages.

TABLE 1

| Linking Group | Complementary Functionality | Linkage |
|---|---|---|
| —NCS | —NH$_2$ | —NHCSNH— |
| 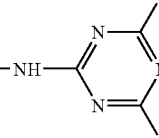 | —NH$_2$ | 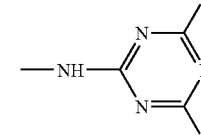 |
| —SO$_2$X | —NH$_2$ | —SO$_2$NH— |
| 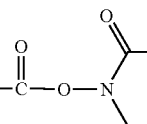 | —NH$_2$ | 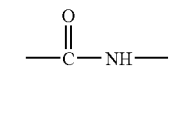 |
| 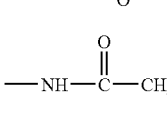 | —SH | 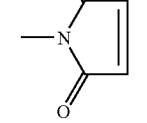 |
| 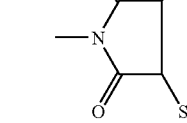 | —SH | |

The term "lower alkyl" denotes straight-chain and branched hydrocarbon moieties containing from 1 to 8 carbon atoms, i.e., methyl, ethyl, propyl, isopropyl, tert-butyl, isobutyl, sec-butyl, neopentyl, tert-pentyl, and the like.

The term "propano" in particular refers to the moiety —CH$_2$CH$_2$CH$_2$—.

"Cycloalkyl" refers to hydrocarbon moieties that form rings, e.g. cyclohexyl and cyclopentyl. Nitrogen atoms with cycloalkyl substituents may form aziridinyl, azetidinyl, pyrrolidinyl, piperidinyl, larger rings, and substituted forms thereof.

"Lower substituted alkyl" denotes a lower alkyl including electron-withdrawing substituents, such as halo, cyano, nitro, sulfo, and the like.

"Lower haloalkyl" denotes a lower substituted alkyl with one or more halogen atom substituents, usually fluoro, chloro, bromo, or iodo.

"Lower alkene" denotes a lower alkyl or lower substituted alkyl wherein one or more of the carbon-carbon bonds is a double bond.

"Lower alkyne" denotes a lower alkyl or lower substituted alkyl wherein one or more of the carbon-carbon bonds is a triple bond.

"Lower Alkoxy" refers to a moiety including lower alkyl single bonded to an oxygen atom.

"Aryl" refers to single or multiple phenyl or substituted phenyl, e.g., benzene, naphthalene, anthracene, biphenyl, and the like.

The term "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1'position, including 2'-deoxy and 2'-hydroxyl forms (Stryer). The term "nucleotide" as used herein refers to a phosphate ester of a nucleoside, e.g., triphosphate esters, wherein the most common site of esterification is the hydroxyl group attached at the C-5 position of the pentose. Many times in the present disclosure the term nucleoside will be intended to include both nucleosides and nucleotides.

"Analogs" in reference to nucleosides include synthetic analogs having modified base moieties, modified sugar moieties, and/or modified phosphate ester moieties, e.g., as described elsewhere (Scheit; Eckstein). The term "labeled nucleoside" refers to nucleosides which are covalently attached to the dye compounds of Formula I.

As used herein, the terms "polynucleotide" or "oligonucleotide" refer to linear polymers of natural nucleotide monomers or analogs thereof including double and single stranded deoxyribonucleotides, ribonucleotides, α-anomeric forms thereof, and the like. Usually the nucleoside monomers are linked by phosphodiester linkages, where as used herein, the term "phosphodiester linkage" refers to phosphodiester bonds or analogs thereof including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like if such counterions are present. Polynucleotides typically range in size from a few monomeric units, e.g. 8-40, to several thousands of monomeric units. Whenever a polynucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted.

As used herein the term "spectral resolution" in reference to a set of dyes means that the fluorescent emission spectra of the dyes are sufficiently distinct, i.e., sufficiently non-overlapping, that reagents to which the respective dyes are attached, e.g., polynucleotides, can be distinguished on the basis of the fluorescent signal generated by the respective dyes using standard photodetection systems, e.g., employing a system of band pass filters and photomultiplier tubes, a charged-coupled device in conjunction with a spectrograph, or the like, as exemplified by systems described elsewhere (Hunkapiller, Wheeless).

The term "substituted" as used herein refers to a molecule wherein one or more hydrogen atoms are replaced with one or more non-hydrogen atoms, functional groups or moieties. For example, an unsubstituted nitrogen is —$NH_2$, while a substituted nitrogen is —$NHCH_3$. Exemplary substituents include but are not limited to halo, e.g., fluorine and chlorine, lower alkyl, lower alkene, lower alkyne, sulfate, sulfonate, sulfone, amino, ammonium, amido, nitrile, lower alkoxy, phenoxy, aromatic, phenyl, polycyclic aromatic, heterocycle, and linking group.

II. 4,7-Dichlororhodamine Dye Compounds.

In a first aspect, the present invention comprises a novel class of 4,7-dichlororhodamine dye compounds having the general structure shown immediately below as Formula I. (Note that all molecular structures provided throughout this disclosure are intended to encompass not only the exact electronic structure presented, but also include all resonant structures, enantiomers, diastereomers, and protonation states thereof.)

FORMULA I

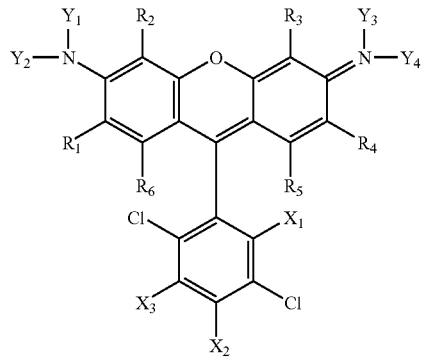

In Formula I, the variable substituents are defined as follows. $R_1$-$R_6$ taken separately are hydrogen, fluorine, chlorine, lower alkyl, lower alkene, lower alkyne, cycloalkyl, phenyl, aryl, sulfonate, sulfone, amino, amido, nitrile, lower alkoxy, linking group, or combinations thereof, or, when taken together, $R_1$ and $R_6$ is benzo, or, when taken together, $R_4$ and $R_5$ is benzo. Preferably, $R_1$-$R_6$ are hydrogen, methyl, or ethyl. $Y_1$-$Y_4$ taken separately are hydrogen, lower alkyl, alkyl sulfonate, alkyl carboxylate, or cycloalkyl. Or, when taken together, $Y_1$ and $R_2$, $Y_2$ and $R_1$, $Y_3$ and $R_3$, and/or $Y_4$ and $R_4$ are propano, ethano, or substituted forms thereof to form fused rings. $X_1$-$X_3$ taken separately are hydrogen, chlorine, fluorine, lower alkyl, carboxylate, sulfonic acid (sulfonate), hydroxymethyl (—$CH_2OH$), and linking groups. Preferably, $X_1$ is carboxylate and $X_2$ and $X_3$ taken separately are hydrogen and linking group.

In a set of particularly preferred compound of the present invention, R is hydrogen (dJON) or methyl (DMDJ), shown below as FORMULA II.

FORMULA II

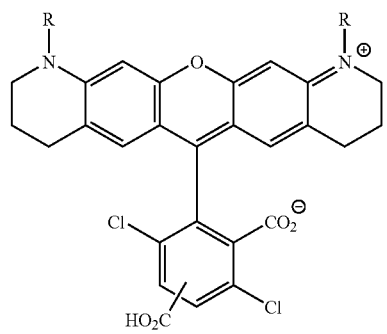

R = H     dJON
R = $CH_3$     DMD

Another particularly preferred compound of the present invention is referred to as dR650, shown below as FORMULA III.

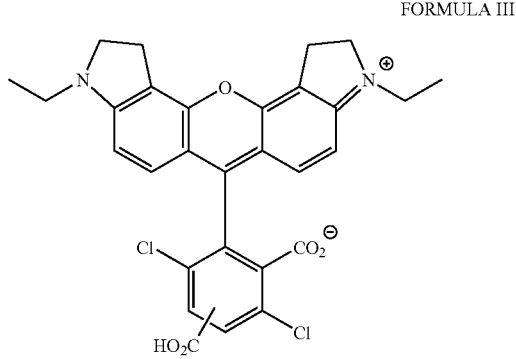

FORMULA III

A third particularly preferred set of compounds are where R is 6-hexanoic acid (dJODA) or methyl-p-benzoic acid (dR134), as shown below in FORMULA IV.

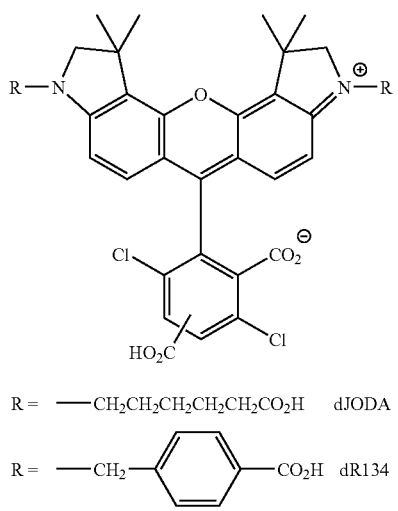

FORMULA IV

R = —CH₂CH₂CH₂CH₂CH₂CO₂H   dJODA

R = —CH₂—⟨phenyl⟩—CO₂H   dR134

A fourth particularly preferred compound of the present invention is referred to herein as dR139, where $Y_1$ and $Y_2$, and $Y_3$ and $Y_4$, form pyrrolidinyl rings as nitrogen substituents, $R_{1-6}$ are hydrogen, $X_1$ is carboxyl, and $X_2$ and $X_3$ are carboxyl and hydrogen. The structure of dR139 is shown below as Formula V.

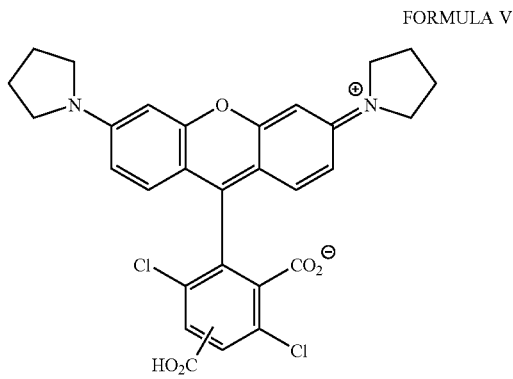

FORMULA V

In a second aspect, the present invention comprises a novel class of 4,7-dichlororhodamie dye compounds having the general structure shown below as FORMULA VI.

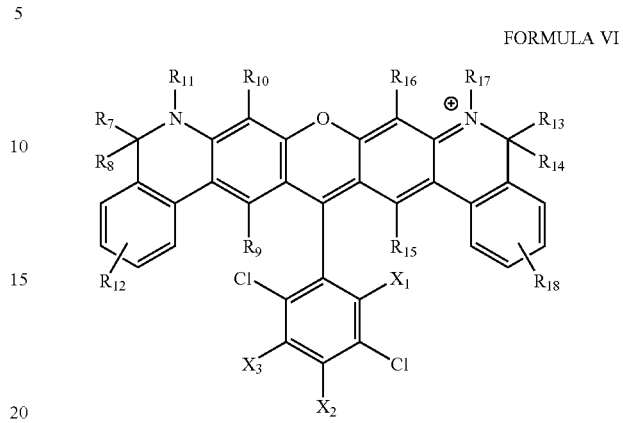

FORMULA VI

In Formula VI, $R_7$-$R_{10}$, $R_{12}$-$_{16}$, and $R_{18}$ may be hydrogen, fluorine, chlorine, methyl, ethyl, lower alkyl, lower alkene, lower alkyne, cycloalkyl, phenyl, aryl, sulfonate, sulfone, amino, amido, nitrile, lower alkoxy, linking group, or combinations thereof. Preferably, $R_7$-$R_{10}$ and $R_{13}$-$R_{16}$ are hydrogen, methyl, or ethyl. $R_7$ and $R_8$, or $R_{13}$ and $R_{14}$, taken together may be oxygen (=O), sulfur (=S), imminium (=NH), alkylimminium (=NR). $R_{11}$ and $R_{17}$ may be hydrogen, lower alkyl, alkyl sulfonate, alkyl carboxylate, lower alkene, lower alkyne, cycloalkyl, phenyl, aryl, linking group, or combinations thereof. Preferably $R_{11}$ and $R_{17}$ are methyl or phenyl. $X_1$-$X_3$ taken separately are hydrogen, chlorine, fluorine, lower alkyl, amine, amide, carboxylate, sulfonic acid (sulfonate), hydroxymethyl (—CH₂OH), and linking groups. Preferably, $X_1$ is carboxylate and $X_2$ and $X_3$ taken separately are hydrogen or linking group. Particular preferred embodiments are where $R_7$, $R_8$, $R_{10}$ $R_{13}$, $R_{14}$, and $R_{17}$ are hydrogen or methyl, $R_9$ and $R_{15}$ are hydrogen, $R_{11}$ and $R_{15}$ are methyl or phenyl, and $R_{12}$ and $R_{18}$ are hydrogen.

III. Reagents Utilizing 4,7-Dichlororhodamine Dye Compounds

In another aspect, the present invention comprises reagents labeled with the 4,7-dichlororhodamine dye compounds of Formulas I-VI. Reagents of the invention can be virtually anything to which the dyes of the invention can be attached. Preferably the dyes are covalently attached to the reagent directly or through a linkage. Exemplary reagents include proteins, polypeptides, polysaccharides, nucleotides, nucleosides, polynucleotides, lipids, solid supports, organic and inorganic polymers, and combinations and assemblages thereof, such as chromosomes, nuclei, living cells, such as bacteria, other microorganisms, mammalian cells, tissues, glycoproteins, and the like.

A. Nucleotide Reagents

A preferred class of reagents of the present invention comprise nucleotides and nucleosides which incorporate the asymmetric benzoxanthene dyes of the invention. Such nucleotide/side reagents are particularly useful in the context of labeling polynucleotides formed by enzymatic synthesis, e.g., nucleotide triphosphates used in the context of PCR amplification, Sanger-type polynucleotide sequencing, and nick-translation reactions.

Preferred nucleotide/side reagents of the present invention are shown below in Formula VII wherein

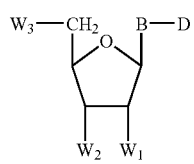

FORMULA VII

B is a nucleoside base; 7-deazapurine, purine, or pyrimidine nucleotide base, analogs thereof, and preferably uracil, cytosine, deazaadenine, or deazaguanosine. D is the 4,7-dichlororhodamine dye compound of the Formulas I-VI of the invention. $W_1$ and $W_2$ taken separately are H or OH. $W_3$ is OH, $OPO_3$, $OP_2O_6$, $OP_3O_9$, including analogs thereof, e.g., phosphorothioate, phosphoroanilidate, phosphoroanilothioate, phosphoramidiate, and other like phosphate analogs, including associated counterions if present, e.g., $H^+$, $Na^+$, $NH_4^+$, and the like. In one preferred embodiment, $W_1$ is H, $W_2$ is OH, and $W_3$ is $OP_3O_9$. In a second preferred embodiment, $W_1$ and $W_2$ are H and $W_3$ is $OP_3O_9$. When B is purine or 7-deazapurine, the sugar moiety is attached at the $N^9$-position of the purine or deazapurine, and when B is pyrimidine, the sugar moiety is attached at the $N^1$-position of the pyrimidine. The linkage linking B and D is attached to D at one of positions $R_1$-$R_{18}$ or $X_1$-$X_3$.

When B is purine or 7-deazapurine, the sugar moiety is attached at the $N^9$-position of the purine or deazapurine, and when B is pyrimidine, the sugar moiety is attached at the $N^1$-position of the pyrimidine.

The linkage linking B and D may be attached to D at any one of positions $R_1$-$R_{18}$ or $X_1$-$X_3$. Preferably, the linkage is attached at one of $X_2$ or $X_3$. Preferably, when B is a purine, the linkage linking B and D is attached to the 8-position of the purine, when B is 7-deazapurine, the linkage is attached to the 7-position of the 7-deazapurine, and when B is pyrimidine, the linkage is attached to the 5-position of the pyrimidine.

In one particularly preferred embodiment, the nucleotides of the present invention are dideoxynucleotide triphosphates having the structure shown below in Formula VIII, including associated counterions if present.

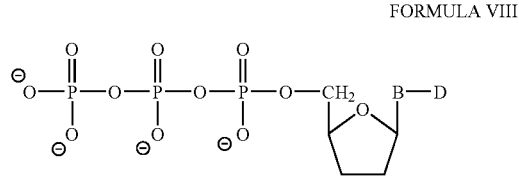

FORMULA VIII

Labeled dideoxy nucleotides such as that shown in Formula VIII find particular application as chain terminating agents, or "terminators", in Sanger-type DNA sequencing methods (Sanger).

In a second particularly preferred embodiment, the nucleotides of the present invention are deoxynucleotide triphosphates having the structure shown in Formula IX below, including associated counterions if present.

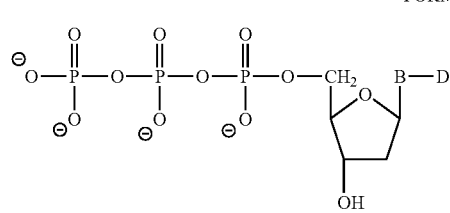

FORMULA IX

Labeled deoxynucleotides such as that shown in Formula IX find particular application as means for labeling polymerase extension products, e.g., in the polymerase chain reaction (Mullis).

Nucleotide/side labeling can be accomplished using any of a large number of known nucleoside/tide labeling techniques using known linking groups, and associated complementary functionalities to form linkages. See above for a discussion of preferred linking groups. The linkage linking the dye and nucleoside should (i) not interfere with oligonucleotide-target hybridization, (ii) be compatible with relevant enzymes, e.g., polymerases, ligases, and the like, and (iii) not quench the fluorescence of the dye.

In one preferred embodiment, the dyes of the invention are covalently linked to the 5-carbon of pyrimidine bases or to the 7-carbon of 7-deazapurine bases. Several suitable base labeling procedures have been reported that can be used with the invention. (Gibson; Gebeyehu; Haralambidis; Nelson 1992; Bergstrom; Fung 1988; Ward; Woo.)

Preferably, the linkages are acetylenic amido or alkenic amido linkages, the linkage between the dye and the nucleotide base being formed by reacting an activated NHS ester of the dye with an alkynylamino- or alkenylamino-derivatized base of a nucleotide. More preferably, the resulting linkage is 3-carboxy)amino-1-propynyl or 3-amino-1-propyn-1-yl (Formula X.1). Several preferred linkages for linking the dyes of the invention to a nucleoside base are shown below as Formulas X.1-6 (Khan).

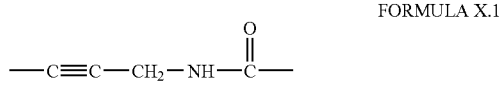

FORMULA X.1

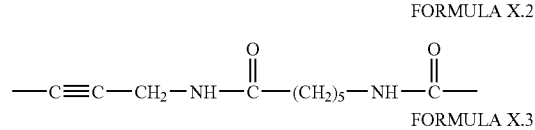

FORMULA X.2

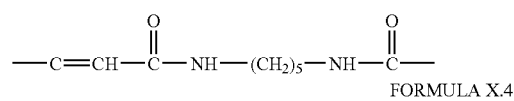

FORMULA X.3

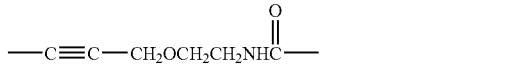

FORMULA X.4

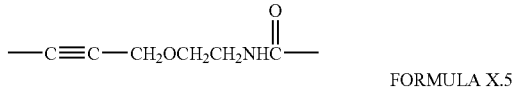

FORMULA X.5

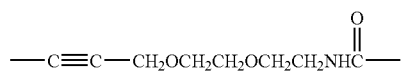

-continued

FORMULA X.6

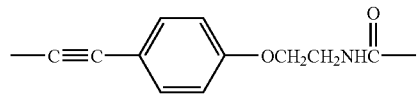

The synthesis of alkynylamino-derivatized nucleosides is described by (Hobbs 1989, 1992). Briefly, the alkynylamino-derivatized nucleotides are formed by placing the appropriate halodideoxynucleoside (usually 5-iodopyrimidine and 7-iodo-7-deazapurine dideoxynucleosides) and Cu(I) in a flask, flushing with argon to remove air, adding dry DMF, followed by addition of an alkynylamine, triethylamine and Pd°. The reaction mixture is stirred for several hours, or until thin layer chromatography indicates consumption of the halo-dideoxynucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The 5'-triphosphates are obtained by standard techniques.

B. Polynucleotide Reagents

Yet another preferred class of reagents of the present invention comprise polynucleotides labeled with the 4,7-dichlororhodamine dyes of the invention. Such labeled polynucleotides are useful in a number of important contexts including as DNA sequencing primers, PCR primers, oligonucleotide hybridization probes, and the like.

The polynucleotides of the invention include a nucleotide having the formula:

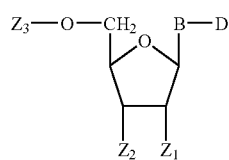

FORMULA XI wherein the variable substituents and linkages are defined as follows. D is a 4,7-dichlororhodamine dye compound of the invention. B is a 7-deazapurine, purine, or pyrimidine nucleotide base, preferably uracil, cytosine, deazaadenine, or deazaguanosine. $Z_1$ is H, OH, or $OCH_3$. $Z_2$ is H, OH, $OPO_3$, $OP_2O_6$, $OP_3O_9$, or Nuc, a neighboring nucleotide, wherein Nuc and the nucleoside are linked by a phosphodiester linkage or analog thereof, e.g., phosphorothioate, phosphoroanilidate, phosphoroanilothioate, phosphoramidiate, and other like phosphate analogs, including associated counterions if present, e.g., $H^+$, $Na^+$, $NH_4^+$, the linkage being attached to the 5'-position of Nuc. $Z_3$ is H, $OPO_2$, including phosphate analogs, or Nuc, wherein Nuc and the nucleoside are linked by a phosphodiester linkage or analog thereof, the linkage being attached to the 3'-position of Nuc wherein Nuc refers to a nucleoside, nucleotide, or polynucleotide. When B is purine or 7-deazapurine, the sugar moiety is attached at the $N^9$-position of the purine or deazapurine, and when B is pyrimidine, the sugar moiety is attached at the $N^1$-position of the pyrimidine. B is attached to the sugar moiety and to the dye compound as described above for the nucleotide reagent of the invention. As defined, the labeled nucleotide of Formula XI can be the 5'-terminal nucleotide, the 3'-terminal nucleotide, or any internal nucleotide of the polynucleotide.

In one preferred embodiment, the polynucleotide of the present invention includes multiple dyes, at least one of which is a dye compound of the invention, located such that fluorescence energy transfer takes place between a donor dye and an acceptor dye. Such multi-dye polynucleotides find application as spectrally-tunable probes or DNA sequencing primers (Ju; Lee).

Labeled polynucleotides may be synthesized either enzymatically, e.g., using a DNA polymerase or ligase (Stryer), or by chemical synthesis, e.g., by the phosphoramidite method, the phosphite-triester method, and the like (Gait). Labels may be introduced during enzymatic synthesis utilizing labeled nucleotide triphosphate monomers as described above or may be introduced subsequent to synthesis.

Generally, if the labeled polynucleotide is made by enzymatic synthesis, the following procedure may be used. A template DNA is denatured and an oligonucleotide primer is annealed to the template DNA. A mixture of deoxynucleotide triphosphates and/or dideoxynucleotide triphosphates is added to the reaction including dGTP, dATP, dCTP, ddTTP, ddGTP, ddATP, ddCTP, and ddTTP, where at least a fraction of one of at least one the deoxynucleotides and/or dideoxynucleotides is labeled with a dye compound of the invention as described above. Next, a polymerase enzyme is added under-conditions where its polymerase activity is operative. A labeled polynucleotide is formed by the incorporation of the labeled deoxynucleotides and/or dideoxynucleotides during polymerase strand synthesis. In an alternative enzymatic synthesis method, two primers are used instead of one, one primer complementary to the + (plus) strand and the other complementary to the − (minus) strand of the target, the polymerase is a thermostable polymerase, and the reaction temperature is cycled between a denaturation temperature and an extension temperature, thereby exponentially synthesizing a labeled complement to the target sequence by PCR (Mullis; Innis).

Subsequent to synthesis, the polynucleotide may be labeled at a number of positions including the 5'-terminus (Eckstein; Orgel; Smith); the phosphodiester backbone (Eckstein); or at the 3'-terminus (Nelson 1992a; Nelson 1992b; Nelson 1995). For a through review of oligonucleotide labeling procedures see (Steiner).

In one preferred post-synthesis chemical labeling method an oligonucleotide is labeled as follows. A dye including a carboxylate linking group is converted to the NHS ester by reacting with approximately 1 equivalent of 1,3-dicyclohexylcarbodiimide and approximately 3 equivalents of N-hydroxysuccinimide in dry ethyl acetate for 3 hours at room temperature. The reaction mixture is washed with 5% HCl, dried over magnesium sulfate, filtered, and concentrated to a solid which is resuspended in DMSO. The DMSO dye stock is then added in excess (10-20×) to an aminohexyl derivatized oligonucleotide in 0.25 M bicarbonate/carbonate buffer at pH 9.4 and allowed to react for 6 hours (Fung 1988). The dye labeled oligonucleotide is separated from unreacted dye by passage through a size-exclusion chromatography column eluting with buffer, e.g., 0.1 molar triethylammonium acetate (TEAA). The fraction containing the crude labeled oligonucleotide is further purified by reverse phase HPLC employing gradient elution.

IV. Methods Utilizing Compounds and Reagents of the Invention

The dyes and reagents of the present invention are well suited to methods utilizing fluorescent detection, particularly methods requiring the simultaneous detection of multiple spatially-overlapping analytes. Dyes and reagents of the invention are particularly well suited for identifying classes of polynucleotides that have been subjected to a biochemical separation procedure, such as electrophoresis, where a series of bands or spots of target substances having similar physiochemical properties, e.g. size, conformation, charge, hydrophobicity, or the like, are present in a linear or planar arrangement. As used herein, the term "bands" includes any spatial grouping or aggregation of analytes on the basis of similar or identical physiochemical properties. Usually bands arise in the separation of dye-polynucleotide conjugates by electrophoresis.

Classes of polynucleotides can arise in a variety of contexts. In a preferred category of methods referred to herein as "fragment analysis" or "genetic analysis" methods, labeled polynucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography; and, the separated fragments are detected subsequent to the separation, e.g., by laser-induced fluorescence. In a particularly preferred embodiment, multiple classes of polynucleotides are separated simultaneously and the different classes are distinguished by spectrally resolvable labels.

One such fragment analysis method known as amplified fragment length polymorphism detection (AmpFLP) is based on amplified fragment length polymorphisms, i.e., restriction fragment length polymorphisms that are amplified by PCR (Vos). These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled polynucleotide PCR primer, or by utilizing labeled nucleotide triphosphates in the PCR.

Another exemplary fragment analysis method is based on variable number of tandem repeats; or VNTRs (Webber; Caskey). VNTRs are regions of double-stranded DNA that contain adjacent multiple copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2-4 bases) repeated sequence. One of the most abundant interspersed repetitive DNA families in humans is the (dC-dA)n-(dG-dT)n dinucleotide repeat family (also called the (CA)n dinucleotide repeat family). There are thought to be as many as 50,000 to 100,000 (CA)n repeat regions in the human genome, typically with 15-30 repeats per block. Many of these repeat regions are polymorphic in length and can therefore serve as useful genetic markers. Preferably, in VNTR or STR methods, a dye label is introduced into the polynucleotide fragments by using a dye-labeled PCR primer.

In a particularly preferred fragment analysis method, classes identified in accordance with the invention are defined in terms of terminal nucleotides so that a correspondence is established between the four possible terminal bases and the members of a set of spectrally resolvable dyes (Fung 1989). Such sets are readily assembled from the dyes of the invention by measuring emission and absorption bandwidths with commercially available spectrophotometers. More preferably, the classes arise in the context of the chemical or chain termination methods of DNA sequencing, and most preferably the classes arise in the context of the chain termination method, i.e., dideoxy DNA sequencing, or Sanger sequencing. This method involves the synthesis of a DNA strand by a DNA polymerase in vitro using a single-stranded or double-stranded DNA template whose sequence is to be determined. Synthesis is initiated at only the one site where an oligonucleotide primer anneals to the template. The synthesis reaction is terminated by incorporation of a nucleotide analog that will not support continued DNA elongation. The chain-terminating nucleotide analogs are typically 2',3'-dideoxynucleoside 5'-triphosphates (ddNTPs) which lack the 3'-OH group necessary for 3' to 5' DNA chain elongation. When proper proportions of dNPTs (2'-deoxynucleoside 5'-triphosphates) and one of the four ddNTPs are used, enzyme-catalyzed polymerization will be terminated in a fraction of the population of chains at each site where the ddNTP can be incorporated. If labeled primers or labeled ddNTPs are used for each reaction, the sequence information can be detected by fluorescence after separation by high-resolution electrophoresis. In the chain termination method, dyes of the invention can be attached to either sequencing primers or dideoxynucleotides.

In each of the above fragment analysis methods labeled polynucleotides are preferably separated by electrophoretic procedures (Rickwood and Hames; Osterman) Preferably the type of electrophoretic matrix is crosslinked or uncrosslinked polyacrylamide having a concentration (weight to volume) of between about 2-20 weight percent. More preferably, the polyacrylamide concentration is between about 4-8 percent. Preferably in the context of DNA sequencing in particular, the electrophoresis matrix includes a strand separating, or denaturing, agent, e.g., urea, formamide, and the like. Detailed procedures for constructing such matrices are given by (Maniatis 1980; *ABI PRISM™ 377 DNA Sequencer User's Manual*). The optimal polymer concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations.

Subsequent to electrophoretic separation, the dye-polynucleotide conjugates are detected by measuring the fluorescence emission from the dye labeled polynucleotides. To perform such detection, the labeled polynucleotides are illuminated by standard means, e.g. high intensity mercury vapor lamps, lasers, or the like. Preferably the illumination means is a laser having an illumination beam at a wavelength between 488 and 550 nm. More preferably, the dye-polynucleotides are illuminated by laser light generated by an argon ion laser, particularly the 488 and 514 nm emission lines of an argon ion laser, or the 532 emission line of a neodymium solid-state YAG laser. Several argon ion lasers are available commercially which lase simultaneously at these lines, e.g., the Model 2001 from Cyonics, Ltd. (Sunnyvale, Calif.). The fluorescence is then detected by a light-sensitive detector, e.g., a photomultiplier tube, a charged coupled device, or the like.

V. EXAMPLES

The invention will be further clarified by a consideration of the following examples, which are intended to be purely exemplary of the invention and not to in any way limit its scope. All reagents were purchased from Aldrich Chemical Co. (Milwaukee, Wis.) except as otherwise indicated. The 3,6-dichlorotrimellitic anhydride was prepared as described by (Khanna).

Example 1

Preparation of dR139:

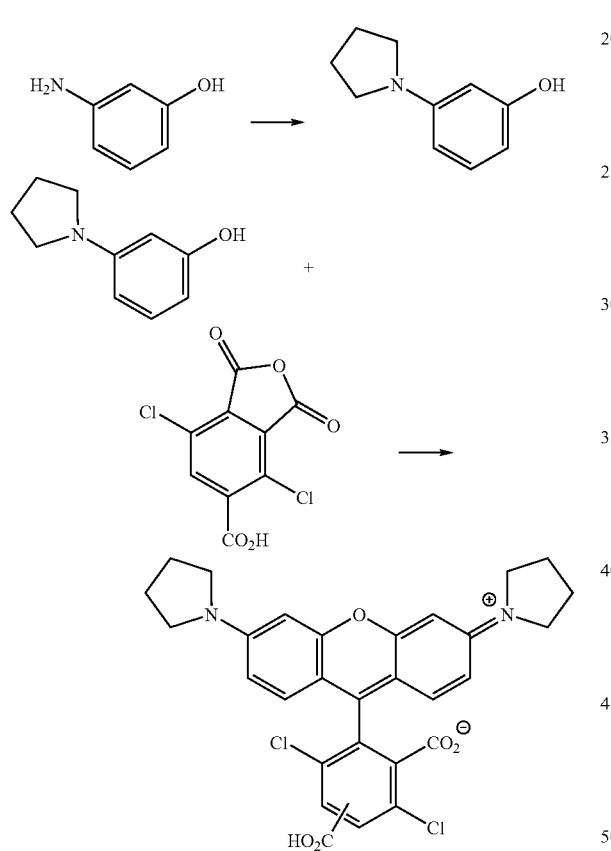

A solution of m-aminophenol (12.6 gm, 0.115 moles) and 1,4-dibromobutane (50 gm, 0.23 moles) was heated to 130° C. for 12 hr. The mixture was cooled to room temperature and triturated with diethylether and then ethyl acetate. The residue was dissolved in ethyl acetate and extracted with 1M NaOH, water, and sat. NaCl. After drying the organic layer with MgSO$_4$, filtering, and evaporating solvent under vacuum, the crude product was purified by silica gel chromatography to give a pale yellow solid. The solid was refluxed with 500 ml toluene and 17 ml triethylamine (0.12 moles) for one hr, cooled to room temperature and washed with water and sat. NaCl. The solution was dried again over MgSO$_4$, filtered, and evaporated under vacuum to give 3-pyrrolidinylphenol as a white solid (6.0 gm, 0.037 moles, 32%).

A mixture of 3-pyrrolidinylphenol (1.63 gm, 10 mmol), 3,6-dichlorotrimellitic anhydride (1.3 g, 5 mmol) and poly-phosphoric acid (5 mL) was heated to 160° C. for 2 hr. After cooling to room temperature, water (20 ml) was added and the precipitated product was collected by filtration. Purification by reverse-phase HPLC separated the 5 and 6 carboxyl isomers of dR139, Abs. max 568 nm (methanol), (Formula V), Isomer 1 (0.3 gm, 5%) and Isomer 2 (0.6 gm, 10%).

Example 2

Synthesis of dR650

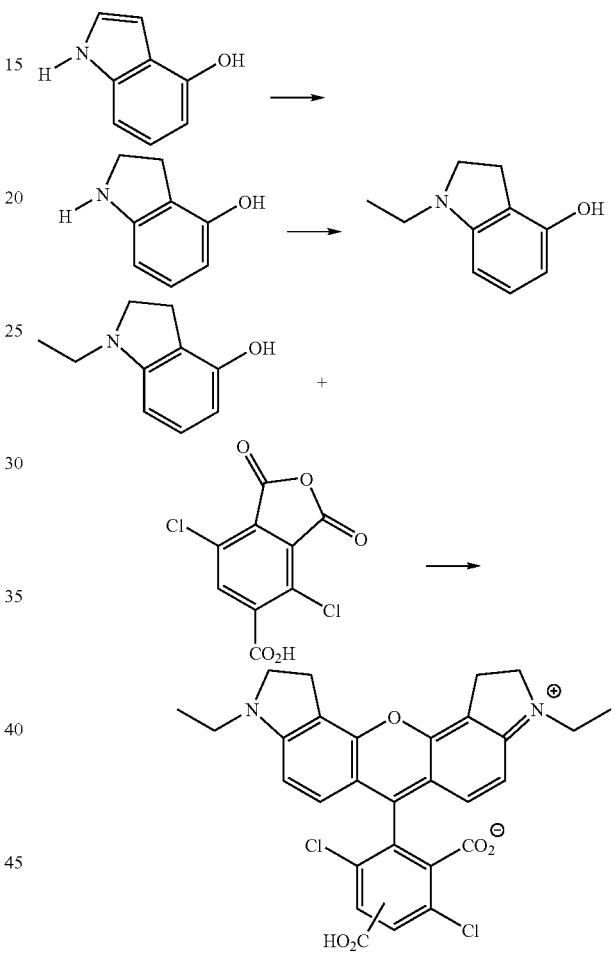

4-Hydroxyindole was reduced with sodium cyanoborohydride and acetic acid to give 4-hydroxy, dihydroindole. A mixture of ethyl iodide (40 ml), potassium carbonate (1.09 gm, 7.8 mmole) and 4-hydroxy, dihydroindole (1.06 gm, 7.8 mmole) was refluxed for 2 hr. Excess ethyl iodide was evaporated under vacuum, water was added (10 ml) and the product was extracted with dichloromethane. Silica gel chromatography gave N-ethyl-4-hydroxy-dihydroindole (0.30 gm, 23% yield) as a pale yellow solid.

A mixture of N-ethyl-4-hydroxy-dihydroindole (0.30 g, 1.8 mmol), 3,6-dichlorotrimellitic anhydride (230 mg, 0.9 mmol) and polyphosphoric anhydride (PPA) (5 g) was heated to 180° C. for 2.5 hr. After cooling to room temperature, the solid was dissolved in aqueous NaOH (1M, 7.5 ml). The product was precipitated with aqueous HCl (2M, 7.5 ml). The solid was collected by filtration and purified by reverse-phase HPLC to give dR650, Em. max, 633 nm (8M urea), Abs. max. 614 nm (8M urea), (FORMULA III). The regiochemistry of the 5 and 6 carboxyl groups of the isomers were not assigned. Isomer 1 (53 mg, 5%) and Isomer 2 (105 mg, 10%) were separable by reverse-phase HPLC.

Example 3

Synthesis of dJON

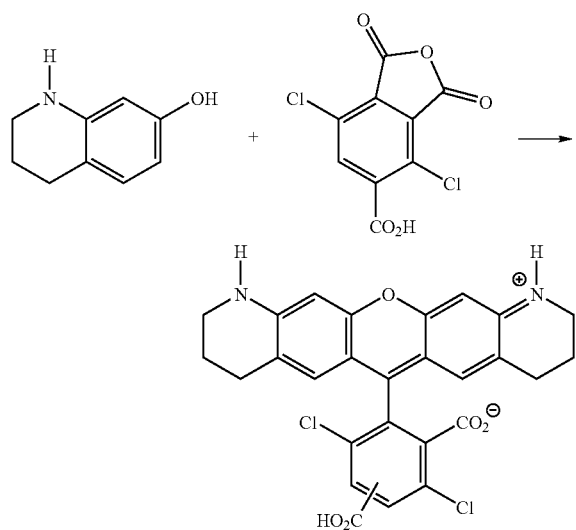

A mixture of 6-hydroxy-1,2,3,4-tetrahydroquinoline (1.49 gm, 10-mmol), 3,6-dichlorotrimellitic anhydride (1.3 g, 5 mmol) and methanesulfonic acid (2 ml) was heated to 160° C. for 6 hr. After cooling to room temperature, water (20 ml) was added and the precipitated product was collected by filtration. Purification by reverse-phase HPLC separated the 5 and 6 carboxyl isomers of dJON, Abs. max 557 nm (methanol), (Formula II), Isomer 1 (270 mg, 5%) and Isomer 2 (550 mg, 10%).

Example 4

Synthesis of Formula VI

A solution of O-fluoro-benzoyl chloride (1.59 gm, 10 mmole) in 2 ml dichloromethane was added dropwise to m-N-methylamino phenol (1.23 gm, 10 mmole) in 5 ml dichloromethane and triethylamine (1.01 g, 1 mmole) cooled in an ice bath. The reaction was allowed to warm to room temperature over one hour. The mixture was diluted with dichloromethane, extracted with water and sat. NaCl, dried with $MgSO_4$, filtered, and evaporated under vacuum. The crude product was purified by silica gel chromatography to give N-methyl, N-(m-hydroxyphenyl)-O-fluoro-benzamide as a white foam (1.2 gm, 5 mmole, 50%).

Sodium hydride (200 mg, 60% dispersion in oil, 5 mmol) was added to the amide (1.2 gm, 5 mmole) in 10 ml dimethylformamide at ambient temperature. The mixture was then refluxed for 2 hours and cooled to room temperature. Solvent was evaporated under vacuum and 5 ml hydrochloric acid (2M) was added. The mixture was extracted with ethyl acetate twice. The combined ethyl acetate extracts were washed with water and sat. NaCl, dried with MgSO4, filtered, and evaporated under vacuum. The crude product was purified by silica gel chromatography to give the cyclized, tricyclic amide as a white solid (0.56 gm, 2.5 mmole, 50%).

Dimethyl sulfide/borane complex (3.75 ml, 7.5 mmole, 2M in THF) was added dropwise to the tricyclic amide (0.56 gm, 2.5 mmole) in 10 ml dry tetrahydrofuran cooled in an ice bath. The mixture was refluxed for one hour, cooled in an ice bath, and 10 ml methanol was added slowly. Solvent was evaporated under vacuum, more methanol was added, and evaporation was repeated thoroughly under vacuum. The crude product was purified by silica gel chromatography to give the tricyclic amine as a white solid (400 mg, 1.9 mmol, 76%).

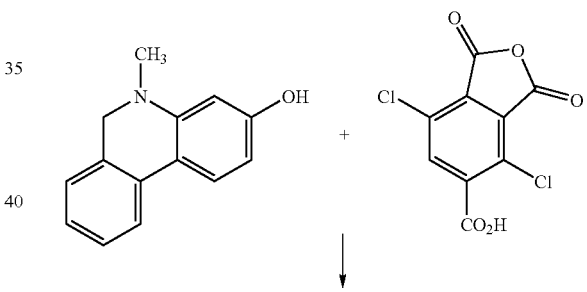

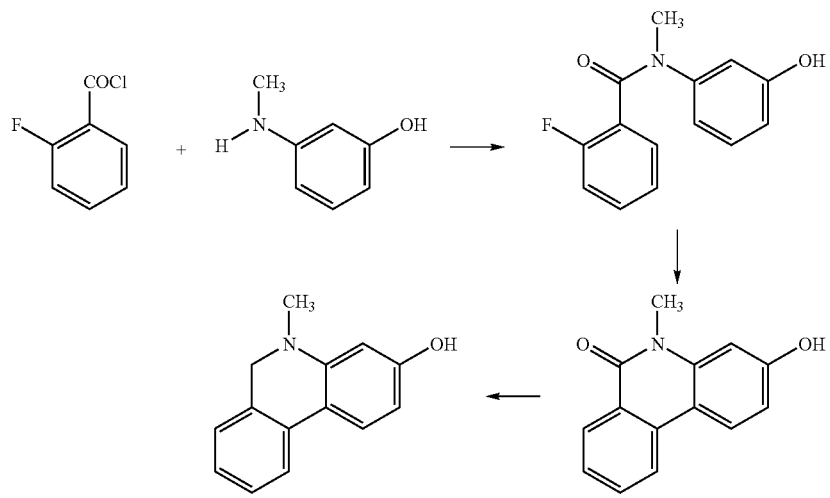

-continued

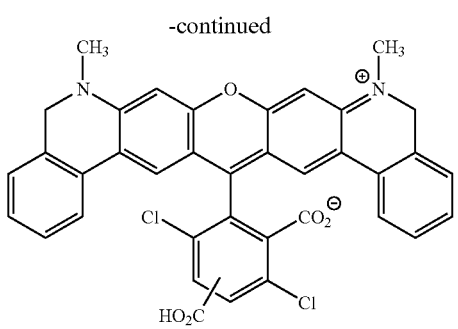

A mixture of the tricyclic amine (400 mg, 1.9 mmol), 3,6-dichlorotrimellitic anhydride (248 mg, 0.95 mmol) and polyphosphoric acid (1 g) was heated to 180° C. for 2 hr. After cooling to room temperature, the solid was dissolved in aqueous NaOH (1M, 7.5 ml). The product was precipitated with aqueous HCl (2M, 7.5 ml). The solid was collected by filtration and purified by reverse-phase HPLC to give the dye, Abs. max 638 nm). The regiochemistry of the 5 and 6 carboxyl groups of the isomers were not assigned. Isomer 1 (32 mg, 5%) and Isomer 2 (65 mg, 10%) were separable by reverse-phase HPLC.

Example 5

Preparation of dR139-Labeled Dideoxyadenosinetriphosphate, Formula VIII

A solution of ddATP-NH$_2$ (5 μL, 20 mM, 0.1 μmol) (Hobbs 1989, 1992), dR139-NHS (0.15 μmol) and 250 mM carbonate/bicarbonate buffer, pH 9 (5 μL) were mixed. After 10 min at room temperature the solution was subjected to HPLC with an anion-exchange column and eluted with a gradient of 40% acetonitrile/60% 0.1 M triethylammonium bicarbonate to 40% acetonitrile/60% 1.5 M triethylammonium bicarbonate to remove free dye. The fraction containing dye-labeled nucleotide and unlabeled nucleotide was concentrated in a vacuum centrifuge and subjected to a second HPLC using a reverse-phase column. The unlabeled nucleotide and each, dye isomer of dye-labeled nucleotide were separated using an elution gradient of 15% acetonitrile/85% 0.1 M triethylammonium acetate to 35% acetonitrile/65% 0.1 M triethylammonium acetate. The solutions containing dye-labeled nucleotide were concentrated in a vacuum centrifuge, redissolved in 10 mM carbonate/bicarbonate buffer, pH 9, and quantified by measuring the absorbance of the solution in a UV/Visible spectrophotometer. Yields were approximately 1%.

Example 6

Preparation of Dye-Labeled Oligonucleotide, Formula XI

A solution of 5'-aminohexyl-functionalized oligonucleotide, (10 μL, 1 mM) and dR139-NHS (10 μl, 12 mM in methylsulfoxide) and carbonate/bicarbonate buffer (2 μL, 1 M) were combined. The aminohexyl derivatized primer was prepared by automated solid-phase DNA synthesis using Aminolink-2 in the last cycle of the synthesis (PE Biosystems). After 10 min at room temperature the solution was subjected to gel filtration on Sephadex G-25 to separate free dye. The fraction containing dye-labeled oligonucleotide and unlabeled oligonucleotide was collected and subjected to HPLC purification on a reverse-phase column. The unlabeled oligonucleotide and each dye isomer of dye-labeled oligonucleotide were separated using an elution gradient of 10% acetonitrile/85% 0.1 M triethylammonium acetate to 30% acetonitrile/65% 0.1 M triethylammonium acetate. The solutions containing dye-labeled oligonucleotide were concentrated in a vacuum centrifuge, and redissolved in a buffer containing 10 mM Tris, 1 mM EDTA, pH 7.0 (TE).

Example 7

Sequencing Reactions Utilizing the 4,7-Dichlororhodamine Dideoxynucleotide Terminators of the Invention Dye terminator reactions were conducted with AmpliTaq® DNA Polymerase, FS following the basic protocols in the ABI PRISM™ Dye Terminator Cycle Sequencing Core-Kit Manual (PE Biosystems). (The FS enzyme is a recombinant *thermus aquaticus* DNA polymerase-having two point mutations—G46D and F667Y). All reagents except the dNTP mix and dye terminators were from an ABI PRISM™ Dye Terminator Cycle Sequencing Core Kit (PE Biosystems). A premix of reaction components was prepared as follows, where volumes are on a per reaction basis:

| | |
|---|---|
| 5X Buffer | 4 μl |
| dNTP mix | 1 μl |
| Template: pGEM ®-3Zf(+), 0.2 μg/μL | 5 μl |
| Primer: −21 M13 (forward), 0.8 pmol/μL | 2 μl |
| AmpliTaq DNA Polymerase, FS | 0.5 μl |
| H$_2$O | 2.5 μl |

Reactions were set up in 0.5 ml tubes for the Perkin-Elmer 480 DNA Thermal Cycler (PE Biosystems). Total reaction volumes were 20 μl, including 15 μl of the above reaction premix, an appropriate amount of dye labeled terminator, and water. Dye terminator reactions were set up with either 1 pmole of dye terminator for A and G terminators or with 15 pmole of dye terminator for C and T terminators, with dyes of the present invention. In a few cases, the dye terminators for C or T were at too low a concentration, such that 5 μL resulted in less than 15 pmole of dye terminator. In these cases, 5 μl of dye terminator was used and no water was added to the reaction. 30 μL of mineral oil was added to the top of each reaction volume to reduce evaporation during thermocycling. Reactions were thermocycled for 25 cycles as follows: 96° C. for 30 sec, 50° C. for 15 sec, 60° C. for 4 min; followed by a 4° C. hold cycle.

All reactions were purified by spin-column purification on Centri-Sep spin columns (Princeton Separations, Adelphia, N.J.). Gel material in the column was hydrated with 0.8 mL of deionized water for at least 30 minutes at room temperature. After the columns were hydrated, and it was apparent that no bubbles were trapped in the gel material, the upper-end cap and then the lower-end cap were removed. The column was allowed to drain by gravity. Columns were then inserted into the wash tubes provided in the Centi-Sep kit and centrifuged in a variable speed microcentrifuge (Eppendorf Model 5415) at 1300×g for 2 minutes. Columns were removed from the wash tubes and inserted into sample collection tubes. The reaction mixture was carefully removed from under the oil using a glass pipette and loaded on top of the Centri-Sep column. Columns were centrifuged for 2 minutes. Samples were dried in a vacuum centrifuge.

The dried samples were resuspended in 25 μl of Template. Suppression Reagent (PE Biosystems), vortexed, heated to 95° C. for 2 minutes, cooled on ice, vortexed again, and centrifuged (13,000×g). 10 μl of the purified sample was aliquoted into sample vials adapted for use with the PE ABI PRISM™ 310 Genetic Analyzer (PE Biosystems). Electrophoresis on the Model 310 used a 61 cm long, 50 μm ID uncoated fused silica capillary having a length to the detector of 50 cm. The capillary was filled with a solution of a linear dimethylpolyacrylamide (DMA) sieving polymer (Madabhushi), buffer, and containing nucleic acid denaturants (PE Biosystems). Samples were electrokinetically injected for 30 sec at 2.5 kV. Electrophoresis was performed for 2 hr at 12.2 kV with the capillary temperature maintained at 42° C.

All publications and patent applications are herein incorporated by reference to the same extent as if each individual publication or patent application was specifically and individually indicated to be incorporated by reference.

Although only a few embodiments have been described in detail above, those having ordinary skill in the organic chemical art will clearly understand that many modifications are possible in the preferred embodiment without departing from the teachings thereof. All such modifications are intended to be encompassed within the following claims.

What is claimed is:

1. A labeled nucleotide according to structural formula (VII):

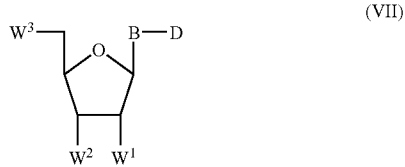

(VII)

wherein:
B is selected from the group consisting of a 7-deazapurine nucleotide base attached to the illustrated furan at its N9 position, a purine nucleotide base attached to the furan of structural formula (VII) at its N9 position and a pyrimidine nucleotide base attached to the furan of structural formula (VII) at its N1 position;
D is a 4,7-dichlororhodamine dye according to structural formula (VI):

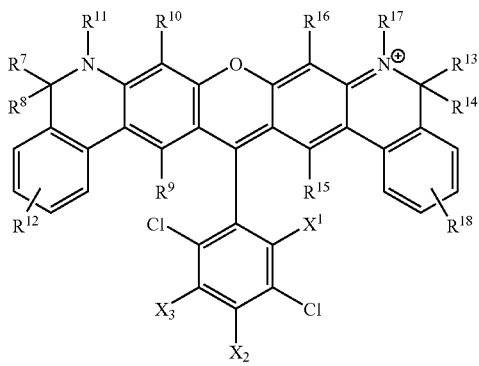

(VI)

wherein:
$R^7$, $R^8$, $R^9$, $R^{10}$, $R^{12}$, $R^{13}$, $R^{14}$, $R^{15}$, $R^{16}$ and $R^{18}$ are each, independently of one another, selected from the group consisting of hydrogen, fluorine, chlorine, methyl, ethyl, lower alkyl, lower alkene, lower alkyne, cycloalkyl, phenyl, aryl, sulfonate, sulfone, amino, amido, nitrile, lower alkoxy and combinations thereof, or, alternatively, $R^7$ and $R^8$ or $R^{13}$ and $R^{14}$ may be taken together for form an oxo, sulfoxo, imminium or alkyliminium group;
$R^{11}$ and $R^{17}$ are each, independently of one another, selected from the group consisting of hydrogen, lower alkyl, alkyl sulfonate, alkyl carboxylate, lower alkene, lower alkyne, cycloalkyl, phenyl, aryl and combinations thereof; and
$X^1$, $X^2$ and $X^3$ are each, independently of one another, selected from the group consisting of hydrogen, chlorine, fluorine, lower alkyl, amine, amide, carboxylate, sulfonate and hydroxymethyl,
with the proviso that one of $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $X^1$, $X^2$ or $X^3$ comprises a linkage linking D to B;
$W^1$ and $W^2$ are each, independently of one another, selected from the group consisting of hydrogen and OH;
$W^3$ is selected from the group consisting of OH, $OPO_3$, $OP_2O_6$, $OP_3O_9$, and analogs thereof.

2. The labeled nucleotide of claim 1 in which D is linked to the 8-position of B when B is a purine nucleotide base, D is linked to the 7-position of B when B is a 7-deazapurine nucleotide base and D is linked to the 5-position of B when B is a pyrimidine nucleotide base.

3. The labeled nucleotide of claim 1 in which $W^3$ is selected from the group consisting of phosphorothioate, phosporoanilidate, phosphoroanilothioate and phosphoramidate.

4. The labeled nucleotide of claim 1 in which $W^1$ is hydrogen, $W^2$ is OH and $W^3$ is $OP_3O_9$.

5. The labeled nucleotide of claim 1 in which $W^1$ and $W^2$ are each hydrogen and $W^3$ is $OP_3O_9$.

6. The labeled nucleotide of claim 1 in which the linkage linking B and D comprises a acetylenic amido or an alkenic amido linkage.

7. The labeled nucleotide of claim 1 in which the linkage linking B and D is selected from the group consisting of —C≡C—CH₂—NH—C(O)—, —C≡C—CH₂—NH—C(O)—(CH₂)₅—NH—C(O)—, —CH═CH—C(O)—NH—(CH₂)₅—NH—C(O)—, —C≡C—CH₂—O—CH₂CH₂—NH—C(O)—, —C≡C—CH₂—O—CH₂CH₂—O—CH₂CH₂—NH—C(O)— and —C≡C—Ph—O—CH₂CH₂—NH—C(O)—, where Ph is 1,4-phenylene.

8. The labeled nucleotide of any one of claims 1-7 in which $X^1$ is carboxylate; one of $X^2$ or $X^3$ is hydrogen and the other one of $X^2$ or $X^3$ comprises the linkage linking D to B.

9. The labeled nucleotide of any one of claims 1-7 in which $R^7$, $R^8$, $R^9$, $R^{10}$, $R^{13}$, $R^{14}$, $R^{15}$ and $R^{16}$ are each, independently of one another, selected from the group consisting of hydrogen, methyl and ethyl.

10. The labeled nucleotide of any one of claims 1-7 in which $R^{11}$ and $R^{12}$ are each, independently of one another, selected from the group consisting of methyl and phenyl.

11. The labeled nucleotide of any one of claims 1-7 in which $R^7$, $R^8$, $R^9$, $R^{10}$, $R^{13}$, $R^{14}$, $R^{15}$ and $R^{16}$ are each, independently of one another, selected from hydrogen, methyl and ethyl.

12. The labeled nucleotide of any one of claims 1-7 in which $R^7$, $R^8$, $R^{10}$, $R^{13}$, $R^{14}$ and $R^{17}$ are each, independently of one another, selected from the group consisting of hydrogen and methyl; $R^9$ and $R^{15}$ are each hydrogen; $R^{11}$ and $R^{16}$ are each methyl or phenyl; and $R^{12}$ and $R^{18}$ are each hydrogen.

13. A labeled polynucleotide containing a nucleotide according to structural formula (XI):

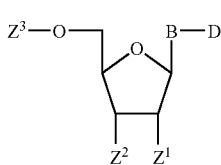

wherein:
B is selected from the group consisting of a 7-deazapurine nucleotide base attached to the illustrated furan at its N9 position, a purine nucleotide base attached to the furan of structural formula (XI) at its N9 position and a pyrimidine nucleotide base attached to the furan of structural formula (XI) at its N1 position;
D is a 4,7-dichlororhodamine dye according to structural formula (VI):

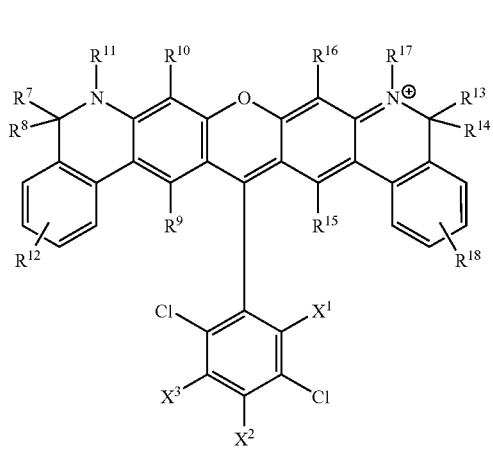

wherein:
$R^7$, $R^8$, $R^9$, $R^{10}$, $R^{12}$, $R^{13}$, $R^{14}$, $R^{15}$, $R^{16}$ and $R^{18}$ are each, independently of one another, selected from the group consisting of hydrogen, fluorine, chlorine, methyl, ethyl, lower alkyl, lower alkene, lower alkyne, cycloalkyl, phenyl, aryl, sulfonate, sulfone, amino, amido, nitrile, lower alkoxy and combinations thereof, or, alternatively, $R^7$ and $R^8$ or $R^{13}$ or $R^{14}$ may be taken together for form an oxo, sulfoxo, imminium or alkyliminium group;
$R^{11}$ and $R^{17}$ are each, independently of one another, selected from the group consisting of hydrogen, lower alkyl, alkyl sulfonate, alkyl carboxylate, lower alkene, lower alkyne, cycloalkyl, phenyl, aryl and combinations thereof; and
$X^1$, $X^2$ and $X^3$ are each, independently of one another, selected from the group consisting of hydrogen, chlorine, fluorine, lower alkyl, amine, amide, carboxylate, sulfonate and hydroxymethyl,
with the proviso that one of $R^7$, $R^8$, $R^9$, R10, $R^{11}$, $R^{12}$, $R^{13}$, $R^{14}$, $R^{15}$, $R^{16}$, $R^{17}$, $R^{18}$, $X^1$, $X^2$ or $X^3$ comprises a linkage linking D to B
$Z^1$ is selected from the group consisting of hydrogen, OH and $OCH_3$;
$Z^2$ is selected from the group consisting of hydrogen, OH, $OPO_3$, $OP_2O_6$, $OP_3O_9$ and $Nuc^1$, where $Nuc^1$ is a nucleosoide, nucleotide or polynucleotide which is linked to structural formula (XI) by a phosphodiester linkage or an analog thereof, the linkage being attached to the 5'-position of $Nuc^1$; and
$Z^3$ is selected from the group consisting of hydrogen, $PO_3$, phosphate analogs and $Nuc^2$, where $Nuc^2$ is a nucleoside, nucleotide or polynucleotide which is linked to structural formula (XI) by a phosphodiester linkage or an analog thereof, the linkage being attached to the 3'-position of $Nuc^2$.

14. The labeled polynucleotide of claim 13 in which D is linked to the 8-position of B when B is a punne nucleotide base, D is linked to the 7-position of B when B is a 7-deazapurine nucleotide base and D is linked to the 5-position of B when B is a pyrimidine nucleotide base.

15. The labeled polynucleotide of claim 13 in which the illustrated nucleotide is a 5'-terminal nucleotide.

16. The labeled polynucleotide of claim 13 in which the illustrated nucleotide is a 3'-terminal nucleotide.

17. The labeled polynucleotide of claim 13 in which the illustrated nucleotide is an internal nucleotide of the polynucleotide.

18. The labeled polynucleotide of claim 13 in which the linkage linking B and D comprises a acetylenic amido or an alkenic amido linkage.

19. The labeled polynucleotide of claim 13 in which the linkage linking B and D is selected from the group consisting of —C≡C—$CH_2$—NH—C(O)—, —C≡C—$CH_2$—NH—C(O)—$(CH_2)_5$—NH—C(O)—, —CH=CH—C(O)—NH—$(CH_2)_5$—NH—C(O)—, —C≡C—$CH_2$—O—$CH_2CH_2$—NH—C(O)—, —C≡C—$CH_2$—O—$CH_2CH_2$—O—$CH_2CH_2$—NH—C(O)— and —C≡C—Ph—O—$CH_2CH_2$—NH—C(O)—, where Ph is 1,4-phenylene.

20. The labeled nucleotide of any one of claims 13-19 in which $X^1$ is carboxylate; one of $X^2$ or $X^3$ is hydrogen and the other one of $X^2$ or $X^3$ comprises the linkage linking D to B.

21. The labeled polynucleotide of any one of claims 13-19 in which $R^7$, $R^8$, $R^9$, $R^{10}$, $R^{13}$, $R^{14}$, $R^{15}$ and $R^{16}$ are each, independently of one another, selected from the group consisting of hydrogen, methyl and ethyl.

22. The labeled nucleotide of any one of claims 13-19 in which $R^{11}$ and $R^{12}$ are each, independently of one another, selected from the group consisting of methyl and phenyl.

23. The labeled nucleotide of any one of claims 13-19 in which $R^7$, $R^8$, $R^9$, $R^{10}$, $R^{13}$, $R^{14}$, $R^{15}$ and $R^{16}$ are each, independently of one another, selected from hydrogen, methyl and ethyl.

24. The labeled nucleotide of any one of claims 13-19 in which $R^7$, $R^8$, $R^{10}$, $R^{13}$, $R^{14}$ and $R^{17}$ are each, independently of one another, selected from the group consisting of hydrogen and methyl; $R^9$ and $R^{15}$ are each hydrogen; $R^{11}$ and $R^{16}$ are each methyl or phenyl; and $R^{12}$ and $R^{18}$ are each hydrogen.

25. A labeled nucleotide according to structural formula (VII):

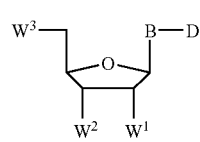

wherein:
B is selected from the group consisting of a 7-deazapurine nucleotide base attached to the illustrated furan at its N9 position, a purine nucleotide base attached to the furan of structural formula (VII) at its N9 position and a pyrimidine nucleotide base attached to the furan of structural formula (VII) at its N1 position;

D is a 4,7-dichlororhodamine dye according to structural formula (I):

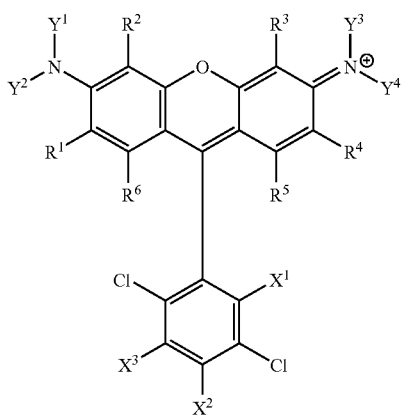

wherein:
$R^1$, $R^2$, $R^3$, $R^4$, $R^5$ and $R^6$, when taken alone, are each, independently of one another, selected from the group consisting of hydrogen, fluorine, chlorine, lower alkyl, lower alkene, lower alkyne, cycloalkyl, phenyl, aryl, sulfonate, sulfone, amino, amido, nitrile, lower alkoxy and combinations thereof, or, alternatively, $R^1$ and $R^2$ and/or $R^4$ and $R^5$ are taken together to form a benzo group;

$Y^1$, $Y^2$, $Y^3$ and $Y^4$, when taken alone, are each, independently of one another, selected from the group consisting of hydrogen, lower alkyl, alkyl sulfonate, alkyl carboxylate and cycloalkyl, or, alternatively, $Y^1$ and $R^2$, $Y^2$ and $R^1$, $Y^3$ and $R^3$ and/or $Y^4$ and $R^4$, are taken together and are each, independently of one another selected from the group consisting of ethano, propano and substituted forms thereof;

$X^1$, $X^2$ and $X^3$ are each, independently of one another, selected from the group consisting of hydrogen, chlorine, fluorine, lower alkyl, carboxylate, sulfonate and hydroxymethyl, with the proviso that one of $R^1$, $R^2$, $R^3$, $R_4$, $R^5$, $R_6$, $X^1$, $X^2$ or $X^3$ comprises a linkage linking D to B;

$W^1$ and $W^2$ are each, independently of one another, selected from the group consisting of hydrogen and OH;

$W^3$ is selected from the group consisting of OH, $OPO_3$, $OP_2O_6$, $OP_3O_9$, and analogs thereof.

26. The labeled nucleotide of claim 25 in which D is linked to the 8-position of B when B is a purine nucleotide base, D is linked to the 7-position of B when B is a 7-deazapurine nucleotide base and D is linked to the 5-position of B when B is a pyrimidine nucleotide base.

27. The labeled nucleotide of claim 25 in which $W^3$ is selected from the group consisting of phosphorothioate, phosporoanilidate, phosphoroanilothioate and phosphoramidate.

28. The labeled nucleotide of claim 25 in which $W^1$ is hydrogen, $W^2$ is OH and $W^3$ is $OP_3O_9$.

29. The labeled nucleotide of claim 25 in which $W^1$ and $W^2$ are each hydrogen and $W^3$ is $OP_3O_9$.

30. The labeled nucleotide of claim 25 in which the linkage linking B and D comprises a acetylenic amido or an alkenic amido linkage.

31. The labeled nucleotide of claim 25 in which the linkage linking B and D is selected from the group consisting of —C≡C—$CH_2$—NH—C(O)—, —C≡C—$CH_2$—NH—C(O)—$(CH_2)_5$—NH—C(O)—, —CH=CH—C(O)—NH—$(CH_2)_5$—NH—C(O)—, —C≡C—$CH_2$—O—$CH_2CH_2$—NH—C(O)—, —C≡C—$CH_2$—O—$CH_2CH_2$—O—$CH_2CH_2$—NH—C(O)— and —C≡C—Ph—O—$CH_2CH_2$—NH—C(O)—, where Ph is 1,4-phenylene.

32. The labeled nucleotide of any one of claims 25-31 in which $X^1$ is carboxylate; one of $X^2$ or $X^3$ is hydrogen and the other one of $X^2$ or $X^3$ comprises the linkage linking D to B.

33. The labeled nucleotide of any one of claims 25-31 in which $R^2$, $R^3$, $R^5$, $R^6$, $Y^1$ and $Y^3$ are each hydrogen; $Y^2$ and $R^1$ are taken together to form a propano group; $Y^4$ and $R^4$ are taken together to form a propano group; $X^1$ is carboxylate; and one of $X^2$ and $X^3$ is hydrogen and the other comprises the linkage to B.

34. The labeled nucleotide of any one of claims 25-31 in which $R^2$, $R^3$, $R^5$ and $R^6$ are each hydrogen; $Y^1$ and $Y^3$ are each methyl; $Y^2$ and $R^1$ are taken together to form an propane group; $Y^4$ and $R^4$ are taken together to from a propane group; $X^1$ is carboxylate; and one of $X^2$ and $X^3$ is hydrogen and the other comprises the linkage to B.

35. The labeled nucleotide of any one of claims 25-31 in which $R^1$, $R^4$, $R^5$ and $R^6$ are each hydrogen; $Y^2$ and $Y^4$ are each ethyl; $Y^1$ and $R^2$ are taken together to form an ethano group; $Y^3$ and $R^3$ are taken together to form an ethano group; $X^1$ is carboxylate; and one of $X^2$ and $X^3$ is hydrogen and the other comprises the linkage to B.

36. The labeled nucleotide of any one of claims 25-31 in which $R^1$, $R^4$, $R^5$ and $R^6$ are each hydrogen; $Y^2$ and $Y^4$ are each —$(CH_2)_5$—COOH; $Y^1$ and $R^2$ are taken together to form a —$CH_2$—$C(CH_3)_2$— group; $Y^3$ and $R^3$ are taken together to form a —$CH_2$—$C(CH_3)_2$— group; $X^1$ is carboxylate; and one of $X^2$ and $X^3$ is hydrogen and the other comprises the linkage to B.

37. The labeled nucleotide of any one of claims 25-31 in which $R^1$, $R^4$, $R^5$ and $R^6$ are each hydrogen; $Y^2$ and $Y^4$ are each —$CH_2$-Ph—COOH, where Ph is 1,4-phenylene; $Y^1$ and $R^2$ are taken together to form a —$CH_2$—$C(CH_3)_2$— group; $Y^3$ and $R^3$ are taken together to form a —$CH_2$—$C(CH_3)_2$— group; $X^1$ is carboxylate; and one of $X^2$ and $X^3$ is hydrogen and the other comprises the linkage to B.

38. The labeled nucleotide of any one of claims 25-31 in which $R^1$, $R^2$, $R^3$, $R^4$, $R^5$ and $R^6$ are each hydrogen; $Y^1$ and $Y^2$ are taken together to form a butano group; $Y^3$ and $Y^4$ are taken together to form a butano group; $X^1$ is carboxylate; and one of $X^2$ and $X^3$ is hydrogen and the other comprises the linkage to B.

39. A labeled polynucleotide containing a nucleotide according to structural formula (XI):

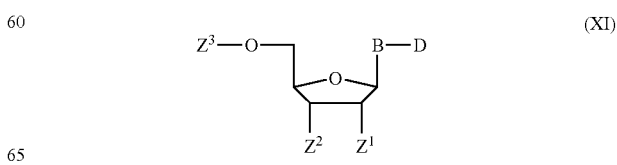

wherein:
- B is selected from the group consisting of a 7-deazapurine nucleotide base attached to the furan of structural formula (XI) at its N9 position, a purine nucleotide base attached to the furan of structural formula (XI) at its N9 position, and a pyrimidine nucleotide base attached to the furan of structural formula (XI) at its N1 position;
- D is a 4,7-dichlororhodamine dye according to structural formula (I):

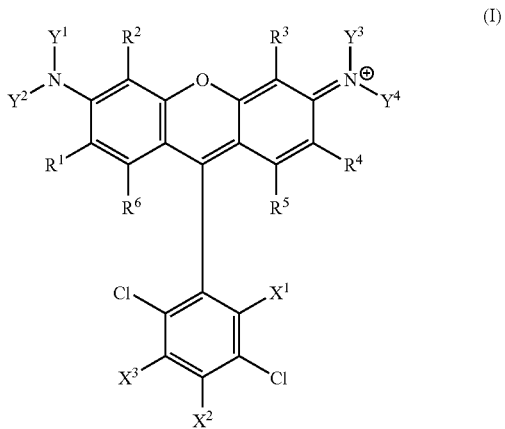

(I)

wherein:
- $R^1, R_2, R^3, R^4, R^5$ and $R^6$, when taken alone, are each, independently of one another, selected from the group consisting of hydrogen, fluorine, chlorine, lower alkyl, lower alkene, lower alkyne, cycloalkyl, phenyl, aryl, sulfonate, sulfone, amino, amido, nitrile, lower alkoxy and combinations thereof, or, alternatively, $R^1$ and $R^6$ and/or $R^4$ and $R^5$ are taken together to form a benzo group;
- $Y^1, Y^2, Y^3$ and $Y^4$, when taken alone, are each, independently of one another, selected from the group consisting of hydrogen, lower alkyl, alkyl sulfonate, alkyl carboxylate and cycloalkyl, or, alternatively, $Y^1$ and $R_2$, $Y^2$ and $R^1$, $Y^3$ and $R^3$ and/or $Y^4$ and $R^4$, are taken together and are each, independently of one another selected from the group consisting of ethano, propano and substituted forms thereof
- $X^1, X^2$ and $X^3$ are each, independently of one another, selected from the group consisting of hydrogen, chlorine, fluorine, lower alkyl, carboxylate, sulfonate and hydroxymethyl,
  with the proviso that one of $R^1, R^2, R^3, R^4, R^5, R^6, X^1, X^2$ or $X^3$ comprises a linkage linking D to B;
- $Z_1$ is selected from the group consisting of hydrogen and OH;
- $Z_2$ is selected from the group consisting of hydrogen, OH, $OPO_3$, $OP_2O_6$, $OP_3O_9$ and $Nuc^1$, where $Nuc^1$ is a nucleoside, nucleotide or polynucleotide which is linked to structural formala (XI) by a phosphodiester linkage or an analog thereof; the linkage being attached to the 5'-position of $Nuc^1$; and
- $Z^3$ is selected from the group consisting of hydrogen, $PO_3$, phosphate analogs and $Nuc^2$, where $Nuc^2$ is a nucleoside, nucleotide or polynucleotide which is linked to structural formal (XI) by a phosphodiester linkage or an analog thereof, the linkage being attached to the 3'-position of $Nuc^2$.

40. The labeled polynucleotide of claim 39 in which D is linked to the 8-position of B when B is a purine nucleotide base, D is linked to the 7-position of B when B is a 7-deazapurine nucleotide base and D is linked to the 5-position of B when B is a pyrimdine nucleotide base.

41. The labeled polynucleotide of claim 39 in which the illustrated nucleotide is a 5'-terminal nucleotide.

42. The labeled polynucleotide of claim 39 in which the illustrated nucleotide is a 3'-terminal nucleotide.

43. The labeled polynucleotide of claim 39 in which the illustrated nucleotide is an internal nucleotide of the polynucleotide.

44. The labeled polynucleotide of claim 37 in which the linkage linking B and D comprises a acetylenic amido or an alkenic amido linkage.

45. The labeled polynucleotide of claim 39 in which the linkage linking B and D is selected from the group consisting of —C≡C—CH₂—NH—C(O)—, —C≡C—CH₂—NH—C(O)—(CH₂)₅—NH—C(O)—, —CH=CH—C(O)—NH—(CH₂)₅—NH—C(O)—, —C≡C—CH₂—O—CH₂CH₂—NH—C(O)—, —C≡C—CH₂—O—CH₂CH₂—O—CH₂CH₂—NH—C(O)— and —C≡C—Ph—O—CH₂CH₂—NH—C(O)—, where Ph is 1,4-phenylene.

46. The labeled nucleotide of any one of claims 39-45 in which $X^1$ is carboxylate; one of $X^2$ or $X^3$ is hydrogen and the other one of $X^2$ or $X^3$ comprises the linkage linking D to B.

47. The labeled nucleotide of any one of claims 39-45 in which $R^2, R^3, R^5, R^6, Y^1$ and $Y^3$ are each hydrogen; $Y^2$ and $R^1$ are taken together to form a propano group; $Y^4$ and $R^4$ are taken together to form a propano group; $X^1$ is carboxylate; and one of $X^2$ and $X^3$ is hydrogen and the other comprises the linkage to B.

48. The labeled nucleotide of any one of claims 39-45 in which $R^2, R^3, R^5$ and $R^6$ are each hydrogen; $Y^1$ and $Y^3$ are each methyl; $Y^2$ and $R^1$ are taken together to form an propane group; $Y^4$ and $R^4$ are taken together to from a propane group; $X^1$ is carboxylate; and one of $X^2$ and $X^3$ is hydrogen and the other comprises the linkage to B.

49. The labeled nucleotide of any one of claims 39-45 in which $R^1, R^4, R^5$ and $R^6$ are each hydrogen; $Y^2$ and $Y^4$ are each ethyl; $Y^1$ and $R^2$ are taken together to form an ethano group; $Y^3$ and $R^3$ are taken together to form an ethano group; $X^1$ is carboxylate; and one of $X^2$ and $X^3$ is hydrogen and the other comprises the linkage to B.

50. The labeled nucleotide of any one of claims 39-45 in which $R^1, R^4, R^5$ and $R^6$ are each hydrogen; $Y^2$ and $Y^4$ are each —(CH₂)₅—COOH; $Y^1$ and $R^2$ are taken together to form a —CH₂—C(CH₃)₂— group; $Y^3$ and $R^3$ are taken together to form a —CH₂—C(CH₃)₂— group; $X^1$ is carboxylate; and one of $X^2$ and $X^3$ is hydrogen and the other comprises the linkage to B.

51. The labeled nucleotide of any one of claims 39-45 in which $R^1, R^4, R^5$ and $R^6$ are each hydrogen; $Y^2$ and $Y^4$ are each —CH₂—Ph—COOH, where Ph is 1,4-phenylene; $Y^1$ and $R^2$ are taken together to form a —CH₂—C(CH₃)₂— group; $Y^3$ and $R^3$ are taken together to form a —CH₂—C(CH₃)₂— group; $X^1$ is carboxylate; and one of $X^2$ and $X^3$ is hydrogen and the other comprises the linkage to B.

52. The labeled nucleotide of any one of claims 39-45 in which $R^1, R^2, R^3, R^4, R^5$ and $R^6$ are each hydrogen; $Y^1$ and $Y^2$ are taken together to form a butano group; $Y^3$ and $Y^4$ are taken together to form a butano group; $X^1$ is carboxylate; and one of $X^2$ and $X^3$ is hydrogen and the other comprises the linkage to B.

* * * * *